United States Patent
Tournilhac et al.

(10) Patent No.: US 7,887,786 B2
(45) Date of Patent: *Feb. 15, 2011

(54) CARE AND/OR MAKE-UP COSMETIC COMPOSITION STRUCTURED WITH SILICONE POLYMERS

(75) Inventors: Florence Tournilhac, Paris (FR); Xavier Blin, Paris (FR)

(73) Assignee: L'Oreal, Paris (FR)

( * ) Notice: Subject to any disclaimer, the term of this patent is extended or adjusted under 35 U.S.C. 154(b) by 714 days.

This patent is subject to a terminal disclaimer.

(21) Appl. No.: 10/538,924

(22) PCT Filed: Dec. 8, 2003

(86) PCT No.: PCT/EP03/15006

§ 371 (c)(1),
(2), (4) Date: Jun. 13, 2005

(87) PCT Pub. No.: WO2004/054523

PCT Pub. Date: Jul. 1, 2004

(65) Prior Publication Data

US 2006/0204470 A1    Sep. 14, 2006

Related U.S. Application Data

(60) Provisional application No. 60/438,782, filed on Jan. 9, 2003.

(30) Foreign Application Priority Data

Dec. 17, 2002    (FR)    .................. 02 16040

(51) Int. Cl.
*A61Q 1/02* (2006.01)
*A61Q 19/04* (2006.01)

(52) U.S. Cl. ........................... 424/63; 514/845; 424/64; 424/70.7; 424/401

(58) Field of Classification Search ................. 424/401, 424/63, 64, 70.7; 514/845
See application file for complete search history.

(56) References Cited

U.S. PATENT DOCUMENTS

| | | | |
|---|---|---|---|
| 2,823,195 A | 2/1958 | Shorr et al. | |
| 2,823,218 A | 2/1958 | Speier et al. | |
| 3,723,566 A | 3/1973 | Thompson et al. | |
| 4,322,400 A | 3/1982 | Yuhas | |
| 4,822,852 A | 4/1989 | Wittmann et al. | |
| 5,262,505 A | 11/1993 | Nakashima et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,512,272 A | 4/1996 | Krzysik | |
| 5,567,428 A | 10/1996 | Hughes | |
| 5,725,882 A | 3/1998 | Kuman et al. | |
| 5,837,223 A | 11/1998 | Barone et al. | |
| 5,851,517 A * | 12/1998 | Mougin et al. ........... 424/78.02 | |
| 5,874,069 A | 2/1999 | Mendolia et al. | |
| 5,919,441 A | 7/1999 | Mendolia et al. | |
| 5,945,095 A * | 8/1999 | Mougin et al. ........... 424/78.02 | |
| 5,969,172 A | 10/1999 | Nye | |
| 5,981,680 A | 11/1999 | Petroff et al. | |
| 5,985,297 A | 11/1999 | Mellul et al. | |
| 6,033,650 A * | 3/2000 | Calello et al. ................. 424/64 | |
| 6,045,782 A | 4/2000 | Krog et al. | |
| 6,051,216 A | 4/2000 | Barr et al. | |
| 6,060,072 A | 5/2000 | Konik et al. | |
| 6,103,250 A | 8/2000 | Brieva et al. | |
| 6,177,091 B1 | 1/2001 | Bara et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |

(Continued)

FOREIGN PATENT DOCUMENTS

EP    0 377 447 A2    7/1990

(Continued)

OTHER PUBLICATIONS

Notice of Rejection for Japanese Patent Application 2004-512707 issued Jun. 6, 2006 (w/English Translation).
U.S. Appl. No. 11/342,748, filed Jan. 31, 2006, Blin, et al.
Notice of Reasons for Rejection from Japanese Application No. 2005-502446, Mailed Jan. 30, 2007, 4 pp.
Dow Corning 2-8178 Gellant, Product Information, Apr. 16, 2003, 6 pages.
U.S. Appl. No. 11/254,919, filed Oct. 21, 2005, Lu, et al.
Dow Corning® 2-8178 Gellant, Ref. No. 27-1055-01, Aug. 2002, 35 pp.

(Continued)

*Primary Examiner*—Johann R Richter
*Assistant Examiner*—Danielle Sullivan
(74) *Attorney, Agent, or Firm*—Oblon, Spivak, McClelland, Maier & Neustadt, L.L.P.

(57) ABSTRACT

Care and/or make-up cosmetic composition comprising: a liquid continuous fatty Phase structured with at least one structuring polymer (homopolymer or copolymer) having a weight-average molecular mass ranging from 500 to 500 000, containing at least one moiety comprising: at least one polyorganosiloxane group consisting of 1 to 1 000 organosiloxane units in the chain of the moiety or in the form of a graft, and at least two groups capable of establishing hydrogen interactions, Chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty Phase at a temperature of 25 to 250° C., the Said liquid fatty Phase comprising at least one compound capable of reducing the enthalpy of fusion of the structuring polymer, and then the liquid fatty Phase, the structuring polymer and the compound capable of reducing the enthalpy of fusion of the structuring polymer forming a physiologically acceptable medium.

45 Claims, No Drawings

U.S. PATENT DOCUMENTS

| | | |
|---|---|---|
| 6,376,078 B1 | 4/2002 | Inokuchi |
| 6,423,324 B1 | 7/2002 | Murphy et al. |
| 6,426,062 B1 | 7/2002 | Chopra et al. |
| 6,451,295 B1 | 9/2002 | Cai et al. |
| 6,503,632 B1 | 1/2003 | Hayashi et al. |
| 6,524,598 B2 | 2/2003 | Sunkel et al. |
| 6,534,072 B2 | 3/2003 | Mondet et al. |
| 6,541,017 B1 | 4/2003 | Lemann et al. |
| 6,569,955 B1 | 5/2003 | Brewer et al. |
| 6,682,748 B1 | 1/2004 | De La Poterie et al. |
| 6,814,973 B2 | 11/2004 | Mondet |
| 6,916,464 B2 | 7/2005 | Hansenne et al. |
| 7,078,026 B2 | 7/2006 | Ferrari et al. |
| 2001/0031280 A1 | 10/2001 | Ferrari et al. |
| 2002/0028223 A1 | 3/2002 | Vatter et al. |
| 2002/0048557 A1 | 4/2002 | Cai et al. |
| 2002/0051758 A1 | 5/2002 | Cai et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235548 A1 | 12/2003 | Lu et al. |
| 2003/0235552 A1 | 12/2003 | Yu |
| 2003/0235553 A1 | 12/2003 | Lu et al. |
| 2004/0001799 A1 | 1/2004 | Lu et al. |
| 2004/0115153 A1 | 6/2004 | Yu |
| 2004/0115154 A1 | 6/2004 | Yu |
| 2004/0120912 A1 | 6/2004 | Yu |
| 2004/0126336 A1 | 7/2004 | Hansenne et al. |
| 2004/0170586 A1 | 9/2004 | Ferrari et al. |
| 2004/0180032 A1 | 9/2004 | Manelski et al. |
| 2004/0197285 A1 | 10/2004 | Van Dort |
| 2004/0223936 A1 | 11/2004 | Fecht et al. |
| 2005/0009989 A1 | 1/2005 | Liew et al. |
| 2005/0020769 A1 | 1/2005 | Lu et al. |
| 2005/0089492 A1 | 4/2005 | Lu et al. |
| 2005/0158260 A1 | 7/2005 | Ferrari et al. |
| 2008/0171008 A1 | 7/2008 | Bui |

FOREIGN PATENT DOCUMENTS

| | | |
|---|---|---|
| EP | 0 594 285 | 4/1994 |
| EP | 0 594 285 A2 | 4/1994 |
| EP | 0 693 517 A1 | 1/1996 |
| EP | 709083 | 5/1996 |
| EP | 0 923 928 | 6/1999 |
| EP | 1 048 686 | 11/2000 |
| EP | 1 068 856 | 1/2001 |
| EP | 1 114 636 | 7/2001 |
| EP | 1 266 647 | 12/2002 |
| EP | 1 266 648 | 12/2002 |
| EP | 1 266 653 | 12/2002 |
| FR | 2 765 800 | 1/1999 |
| FR | 2 825 914 | 12/2002 |
| FR | 2 825 915 | 12/2002 |
| FR | 2 825 916 | 12/2002 |
| GB | 134 8783 | 3/1974 |
| JP | 55-105609 | 8/1980 |
| JP | 02-25411 | 1/1990 |
| JP | 06-279253 | 10/1994 |
| JP | 08-239316 | 10/1994 |
| JP | 09-071505 | 3/1997 |
| JP | 11-236314 | 8/1999 |
| JP | 2000-038450 | 2/2000 |
| JP | 2001-081009 | 3/2001 |
| JP | 2001-81009 | 3/2001 |
| JP | 2001-503070 | 3/2001 |
| JP | 2001-206821 | 7/2001 |
| JP | 2001-512164 | 8/2001 |
| JP | 2001-316244 | 11/2001 |
| JP | 2002-12514 | 1/2002 |
| JP | 2002-173459 | 6/2002 |
| JP | 2002-173460 | 6/2002 |
| JP | 2002-173464 | 6/2002 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO99/22710 | 5/1999 |
| WO | WO 00/09587 | 2/2000 |
| WO | WO 01/09239 A1 | 2/2001 |
| WO | WO 01/97758 A2 | 12/2001 |
| WO | WO 02/17870 A2 | 3/2002 |
| WO | WO 02/17871 A2 | 3/2002 |
| WO | WO 02/089760 A1 | 11/2002 |
| WO | WO 03/013447 A2 | 2/2003 |
| WO | WO 03/105788 A2 | 6/2003 |
| WO | WO 03/101412 A2 | 12/2003 |
| WO | WO 2004/054523 | 7/2004 |
| WO | WO 2004/054524 | 7/2004 |

OTHER PUBLICATIONS

Dow Corning® 2-8178 Gellant, Product Information Personal Care, 6 pp.

Shin-Etsu Silicones for Personal Care; Product Brochure, KSP-100•101•102•103•104•105 "Hybrid Silicone Powders for Personal Care".

Shin-Etsu Silicones for Personal Care; Product Brochure, KSP-200•300 "Hybrid Silicone Powders containing Fluoroalkyl or Phenyl group for Personal Care".

English Language Derwent Abstract of EP 0 923 928, Jun. 23, 1999.

English Language Derwent Abstract of EP 1 068 856, Jan. 17, 2001.

English Language Derwent Abstract of FR 2 765 800, Jan. 15, 1999.

U.S. Appl. No. 11/898,093, filed Sep. 10, 2007, Ferrari, et al.

Notice of Reasons for Rejection from Japanese Application No. 2005-502445, Drafted Jan. 25, 2007, Mailed Jan. 30, 2007, 3 pp.

U.S. Appl. No. 12/648,020, filed Dec. 28, 2009, Yu.

Office Action issued Oct. 5, 2010, in Japanese Application No. 2004-512707 (English Translation).

Office Action dated Oct. 21, 2010, in European Application No. 03739096.0.

\* cited by examiner

US 7,887,786 B2

CARE AND/OR MAKE-UP COSMETIC COMPOSITION STRUCTURED WITH SILICONE POLYMERS

TECHNICAL FIELD

The present invention relates to a care and/or make-up cosmetic composition for the skin, including the hair, and/or the lips of human beings, containing a liquid fatty phase comprising at least one oil, structured with a particular polymer, provided in particular in the form of a cast make-up product, in particular as a make-up stick or dome such as lipsticks, whose application is easy and leads to a substantial, especially coloured, glossy and non-migrating deposit.

A care cosmetic composition is a composition which comprises at least one active compound for, for example, treating wrinkles, for moisturizing the skin and the lips, for protecting the skin, the lips and superficial body growths from ultraviolet rays, for treating acne and/or for acting as self-tanning agent.

The invention relates more particularly to cosmetic and dermatological compositions such as make-up products for easy application and leading to a large deposit and exhibiting properties of staying power, but also of non-transfer and stability.

PRIOR STATE OF THE ART

In cosmetic products, it is common to find a structured, namely gelled and/or rigidified, liquid fatty phase. A composition is rigidified in particular in the case of solid compositions such as balms and lipsticks, eyeshadows, concealer products and foundations which have been cast. This structuring is obtained with the aid of waxes or fillers. Unfortunately, these waxes and fillers tend to mattify the composition; which is not always desirable in particular for a lipstick or an eyeshadow.

The expression liquid fatty phase is understood to mean, for the purposes of the application, a fatty phase which is liquid at room temperature (25° C.) and atmospheric pressure (760 mmHg), which is composed of one or more fatty substances which are liquid at room temperature, which are also called oils, which are compatible with each other.

The expression structured liquid phase is understood to mean a rigidified or gelled liquid fatty phase.

The expression rigified liquid fatty phase is understood to mean, for the purposes of the application, that this rigified phase does not run under its own weight when a silicone polyamide is added thereto.

The expression gelled liquid phase for the purposes of the application is understood to mean that the viscosity of this phase is increased because of the addition of a silicone polyamide to this fatty phase.

The structuring of the liquid fatty phase makes it possible in particular to limit its exudation from solid compositions and, furthermore, to limit, after deposition on the skin or the lips, the migration of this phase into wrinkles and fine lines, which is particularly sought for a lipstick or an eyeshadow. The expression migration is understood to mean an overflowing of the composition deposited on the skin or the lips, outside its initial outline.

The gloss is mainly linked to the nature of the liquid fatty phase. Thus, it is possible to reduce the amount of waxes and fillers in the composition in order to increase the gloss of a lipstick, but then the migration of the liquid fatty phase increases. In other words, the amounts of waxes and fillers necessary for producing a stick of suitable hardness are a barrier to the gloss of the deposit.

The document EP-A-1 068 856 [1] describes solid cosmetic compositions, with no wax, containing a liquid fatty phase structured with a polymer, in which the fatty phase is mainly a non-silicone oil.

The document WO-A-01/97758 [2] describes cosmetic compositions based on polyamide resins comprising a structuring agent chosen from esters and amides of N-acylamino acids and mixtures thereof. The composition also comprises a solvent for the polyamide resin which may be chosen from unsaturated and saturated fatty alcohols, fatty and/or aromatic carboxylic acid esters, ethoxylated and/or propoxylated alcohols and acids, silicones, mineral oils and branched-chain hydrocarbons; preferably, fatty acid esters, fatty alcohols, mineral oils, branched hydrocarbons and mixtures thereof.

The use of fatty phases based on silicone oils makes it possible currently to obtain cosmetic compositions having a long staying power when the oils are only slightly volatile or are non-volatile, namely a good staying power in particular of the colour over time (unchanging, unfading), and transfer-free compositions when the silicone oils are volatile, not forming a deposit on a support such as a glass, a cup, a fabric or a cigarette, placed in contact with the film of make-up.

Currently, the use of silicone oils in cosmetics is limited by the small number of molecules which can gel these media and thus give compositions which exist in solid form such as lipsticks or cast foundations for example. The use of cosmetic compositions whose fatty phase is predominantly siliconized leads, in most cases, to problems of compatibility with the ingredients conventionally used in cosmetics.

In the documents U.S. Pat. No. 5,874,069 [3], U.S. Pat. No. 5,919,441 [4], U.S. Pat. No. 6,051,216 [5], WO-A-02/17870 [6], and WO-A-02/17871 [7], WO-A-99/06473 [12], U.S. Pat. No. 6,353,076 [13], cosmetic compositions such as deodorant sticks or gels, comprising a silicone oily phase gelled with a polysiloxane- and polyamide-based wax, or with a polymer containing siloxane groups and groups capable of hydrogen interactions, have been prepared.

In WO-A-02/17870 [6], it is envisaged to add to the composition another structuring agent, but the quantities added should be low, for example less than 0.5% in the case of hydroxystearic acid, in order to preserve the clarity of the product.

In WO-A-02/17871 [7], it is also envisaged to use a second structuring agent with the silicone polymer in a quantity representing 0.5 to 2% by weight of the composition, and a solvent system comprising a non-silicone organic compound, a volatile silicone and optionally another silicone.

The document EP-A-1 177 784 [8] illustrates a deodorant composition comprising a liquid phase containing, for example, a volatile silicone and optionally a non-volatile silicone and/or a non-silicone hydrophobic organic liquid, structured with an organic compound with amido groups, with optionally one or more polymeric or non-polymeric secondary structuring agents in small proportions. Among the secondary structuring agents, this document mentions polymers having siloxane groups and groups exhibiting hydrogen interactions without giving examples or results on a composition using these polymers.

The sticks obtained by structuring the liquid fatty phase with solely one or more gelling silicone polymers do not exhibit sufficient mechanical resistance to shearing, in particular during the application of the stick to the lips and/or the skin, leading to breaking of the stick.

It is evident from the above that the formulation of polymers such as silicone polyamides (PASi) in compatible fatty media makes it possible to obtain solid make-up systems not requiring the use of waxes, and in particular the structuring of highly, or even completely siliconized systems, which is normally difficult to obtain with wax-type traditional structuring agents.

However, it has been possible to demonstrate that the application of the formulas thus obtained could be difficult and that the deposit was not obtained in a sufficient quantity to allow the making up.

The application and the deposit are all the less satisfactory as the concentration required for obtaining a solid system of sufficient hardness is high.

DISCLOSURE OF THE INVENTION

The aim of the invention is precisely to provide a care or make-up composition for the skin and/or the lips, which makes it possible to overcome the disadvantages and to solve the problems mentioned above. In particular, the aim of the invention is to provide a composition whose application is easy and leads to a large deposit, that is to say a large mass, in any case larger than with prior art compositions. The larger deposit of material gives more "make-up effect", and in particular in the case of pigmented, coloured compositions, the deposit having a more intense colour allows the making up, for example, of the lips.

Surprisingly, the applicant has found that the use of particular polymers combined with one or more compositions capable of reducing the enthalpy of fusion and possibly the melting temperature of these polymers made it possible to structure, in the absence or in the presence of small quantities of wax, the liquid fatty phases, based on silicone oil for example, in the form of a make-up or care product whose application was easy, with in particular excellent slipperiness during application and that this use led to a large deposit, that is to say a large mass, in any case larger than with prior art compositions. The larger deposit of composition gives more "make-up effect", and in particular in the case of pigmented, coloured compositions, the deposit having a more intense colour allows the making up, for example, of the lips, a making up which was not satisfactorily possible or even not at all possible with the prior art compositions.

It was additionally noted, equally surprisingly, that the compositions of the invention, including the combinations cited above, exhibited improved gloss both as regards the product before application and the deposit, if this property is desired. Furthermore, the compositions according to the invention, including the combinations cited above, give a non-migrating film or deposit, which has enhanced properties of staying power, and possibly of non-transfer and which is not sticky to the touch.

The combination of these particular compounds with one or more compounds capable of reducing their enthalpy of fusion ΔH and optionally their melting temperature m.p. makes it possible to obtain gels, in particular solid gels, having a good mechanical strength and an acceptable rheology in order to allow a deposit with a large mass, sufficient to allow the make-up, which additionally has an improved gloss.

Make-up or care cosmetic compositions comprising the combination of a particular polymer according to the invention and a specific compound which is a compound capable of lowering, reducing the enthalpy ΔH and optionally the melting temperature m.p. of the polymer are not described in the prior art.

The effects obtained by virtue of this combination of a particular polymer and a particular compound capable of reducing the enthalpy of fusion and optionally of reducing the melting point of the polymer, in particular the surprising improvement of the ease of application, of the deposited mass, as well as the gloss of the deposit and of the product, do not appear in the prior art documents.

The invention not only applies to make-up products for the lips such as lipsticks, lip pencils and lip glosses, but also to care products for the skin, including the scalp, and the lips, such as sun protection products in stick form for the skin, the face or the lips, or lip balms, to make-up products for the skin, both of the face and of the human body, such as foundations cast as a stick or in a dish, concealer products and temporary tattoo products, to cleansing products, in particular in stick form, and to make-up products for the eyes such as eyeliners, in particular in pencil form, and mascaras, in particular cakes for keratinous fibres (eyelashes, eyebrows, hair).

More precisely, the subject of the invention is a make-up cosmetic composition comprising: a liquid continuous fatty phase structured with at least one structuring polymer (homopolymer or copolymer) having a weight-average molecular mass ranging from 500 to 500 000, containing at least one moiety comprising:

at least one polyorganosiloxane group consisting of 1 to 1 000 organosiloxane units in the chain of the moiety or in the form of a graft, and
  at least two groups capable of establishing hydrogen interactions, chosen from ester, amide, sulphonamide, carbamate, thiocarbamate, urea, urethane, thiourea, oxamido, guanidino and biguanidino groups, and combinations thereof,
  the polymer being solid at room temperature and soluble in the liquid fatty phase at a temperature of 25 to 250° C.,
  the said liquid fatty phase comprising at least one compound capable of reducing the enthalpy of fusion of the structuring polymer,
  the said composition containing at least one pigment, and
  the liquid fatty phase, the structuring polymer and the compound capable of reducing the enthalpy of fusion of the structuring polymer forming a physiologically acceptable medium.

According to the invention, the expression "structuring polymer" is generally understood to mean a polymer which makes it possible to rigidify or to gel the composition by forming hydrogen bonds.

The composition of the invention may be provided in the form of a paste, a solid or a more or less viscous cream. It may be a simple or multiple, in particular an oil-in-water or water-in-oil, water-in-oil-in-water or oil-in-water-in-oil emulsion, or a rigid or soft gel having an oily continuous phase. The simple or multiple emulsion may comprise an aqueous or oily continuous phase optionally containing dispersed lipid vesicles. In particular, it is provided in a form cast as a stick or in a dish and more especially in the form of an oily, in particular anhydrous, rigid gel and in particular of an anhydrous stick. More especially, it is provided in the form of a translucent or opaque rigid gel (according to whether it contains pigments or otherwise), the liquid fatty phase forming the continuous phase. An anhydrous composition will comprise less than 10% by weight of water, for example less than 5% by weight, preferably less than 2% by weight of water.

The structuring of the liquid fatty phase can be modulated according to the nature of the structuring polymer and of the compound capable of reducing the enthalpy and possibly the melting temperature used, and may be such that a rigid structure is obtained in the form of a baton, a stick or a dome, having good mechanical strength and already having a glossy appearance. Especially when they are coloured, these batons make it possible, after easy application, to obtain a glossy deposit, which is in particular coloured, with a large mass, which does not migrate and which has good staying power, in particular of the colour over time. The composition may comprise one or more structuring polymers and one or more compounds which reduce the enthalpy of fusion and optionally the melting temperature of these polymers.

Avantageously, the composition of the invention is a composition for the lips and even better a lipstick composition in particular in stick form.

Liquid Fatty Phase

The liquid fatty phase according to the invention comprises at least one oil generally chosen from hydrocarbon, silicone and fluorinated oils.

An oil is a non-aqueous compound which is immiscible with water.

The liquid fatty phase may comprise at least one volatile oil.

For the purposes of the invention, a volatile oil-advantageously has a flash point preferably of 35 to 135° C. (measured according to the method) or no flash point. The flash point is the temperature at which the vapours emitted by a fuel ignite upon contact with a flame, a spark or a heat source.

Volatile oils advantageously have at room temperature (25° C.) and atmospheric pressure (760 mmHg) a vapour pressure ranging from 0.01 mm to 300 mmHg (1.33 Pa to 40 000 Pa) and even better ranging from 0.05 to 190 mmHg (6.65 Pa to 25 330 Pa).

According to the invention, the volatile oil may be chosen from linear, branched or cyclic silicone oils having a flash point equal to or greater than 40° C. and advantageously greater than the softening point of the gelling system and/or a viscosity of less than 8 cSt, such as linear, branched or cyclic polydimethylsiloxanes (PDMS) having from 3 to 7 silicon atoms.

By way of examples of volatile oils, there may be mentioned the compounds given in Table 1 below.

The composition may contain a non-volatile silicone oil.

The silicone oils of the invention have a viscosity which is advantageously chosen from the range going from 5 to 800 000 cSt at 25° C., preferably from 10 to 500 000 cSt, and even better from 10 to 5 000 cSt.

The non-volatile silicone oils may be polydimethylsiloxanes, polyalkylmethylsiloxanes, dimethicone copolyols, alkylmethicone copolyols, cetyldimethicone, silicones with alkylglyceryl ether groups, silicones with side amine groups and dilauroyltrimethylol propane siloxysilicate. The alkyl groups of these oils have in particular from 2 to 24 carbon atoms.

The non-volatile silicone oils which can be used in the invention may be in particular linear, non-volatile polydimethylsiloxanes (PDMS) which are liquid at room temperature; polydimethylsiloxanes containing alkyl, alkoxy or phenyl groups, which are pendent and/or at the silicone chain end, groups each having from 2 to 24 carbon atoms; phenylated silicones such as phenyltrimethicones, phenyldimethicones, phenyltrimethylsiloxy diphenylsiloxanes, diphenyldimethicones, diphenylmethyldiphenyltrisiloxanes, 2-phenylethyl trimethylsiloxysilicates, fluorinated silicones with one or more group(s) that is (are) pendent or at the chain end having from 1 to 12 carbon atoms of which all or some of the hydrogen atoms are substituted with fluorine atoms, dimethiconols and mixtures thereof.

TABLE 1

| Compound | Flash point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF 96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 cSt) from Dow Corning | 102 | 3 |

In other words, the volatile silicone oil(s) may be chosen for example from the group consisting of the compounds of Table 1, heptamethyloctyltrisiloxane, dodecamethylpentasiloxane and mixtures thereof.

The volatile silicone oil may also be chosen from the group comprising fluorinated silicone oils such as silicones with alkyl and perfluoroalkyl groups, silicones with oxyethylenated/oxypropylenated (EO/PP) side groups and with perfluorinated groups, silicones with perfluorinated side groups and with glycerolated side groups, perfluoroalkylmethylphenylsiloxanes, these oils having a vapour pressure greater than or equal to 0.02 mmHg.

The volatile non-silicone oils may be chosen from the group comprising hydrocarbon oils and volatile esters and ethers such as volatile hydrocarbons such as isododecane and isohexadecane, $C_8$-$C_{16}$ isoparaffins, isohexyl or isodecyl neopentanoates.

The volatile oil may also be chosen from fluorinated oils such as perfluoropolyethers, perfluoroalkanes such as perfluorodecalin, perfluorodamantanes, esters (monoesters, diesters and triesters) of perfluoroalkyl phosphates and fluorinated ester oils.

By way of example of volatile non-silicone oils which can be used in the invention, there may be mentioned the compounds of Table 2 which follows.

TABLE 2

| Compound | Flash point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methyl ether acetate* | 46 |
| Isopar L ($C_{11}$–$C_{13}$ isoparaffin) | 62 |
| Isopar H ($C_{11}$–$C_{12}$ isoparaffin) | 56 |

The liquid fatty phase advantageously contains at least 30%, and even better at least 40% by weight of silicone oil(s) advantageously having a viscosity of less than 1 000 cSt and even better of less than 100 cSt because the silicone polymers used in the invention are more soluble in silicone oils of low viscosity. It may also contain other non-silicone oils or a mixture of non-silicone oils.

When the fatty phase comprises a volatile oil, it advantageously represents from 3 to 89.4%, and even better from 5 to 60%, for example from 5 to 10% of the total weight of the composition.

The liquid fatty phase may also contain other non-silicone oils, for example polar oils such as:

hydrocarbonaceous vegetable oils with a high content of triglycerides consisting of esters of fatty acids and of glycerol in which the fatty acids may have varied chain lengths, it being possible for the latter to be linear or branched, saturated or unsaturated; these oils are in particular wheat germ, maize, sunflower, karite, castor, sweet almond, macadamia, apricot, soybean, rapeseed, cottonseed, lucerne, poppy seed, pumpkin seed, sesame, gourd, avocado, hazelnut, grapeseed or blackcurrant seed, evening primrose, millet, barley, quinoa, olive, rye, safflower, candlenut, passion flower and rose musk oils; or triglycerides of caprylic/capric acids such as those sold by the company Stearines Dubois or those-sold under the names Miglyol 810, 812 and 818 by the company Dynamit Nobel;

synthetic oils or esters of formula $R_aCOOR_b$ in which $R_a$ represents the residue of a linear or branched higher fatty acid containing from 1 to 4.0 and even better from 7 to 19 carbon atoms and $R_b$ represents a branched hydrocarbon chain containing from 1 to 40 and even better from 3 to 20 carbon atoms, with $R_a+R_b \geq 10$ such as, for example, Purcellin oil (ketostearyl octanoate), isononyl isononanoate, $C_{12}$ to $C_{15}$ alcohol benzoate, isopropyl myristate, 2-ethylhexyl palmitate, octanoates, decanoates or ricinoleates of alcohols or of polyalcohols; hydroxylated esters such as isostearyl lactate, diisostearyl malate; and esters of pentaerythritol;

synthetic ethers having from 10 to 40 carbon atoms;

fatty acids such as oleic, linoleic or linolenic acid; and mixtures thereof.

The liquid fatty phase may also contain apolar oils such as linear or branched hydrocarbons or fluorocarbons of synthetic or mineral origin, which are volatile or not, such as volatile oils of paraffin (such as isoparaffins, isododecane) or non-volatile oils of paraffin and its derivatives, petroleum jelly, polydecenes, hydrogenated polyisobutene such as parleam, squalane, and mixtures thereof.

Thus, the invention may be carried out for example with the following different fatty phases:

1) a fatty phase consisting of a mixture of oils comprising at least one nonvolatile silicone oil and at least one volatile silicone oil;

2) a fatty phase consisting of a mixture of oils comprising at least one nonvolatile silicone oil and at least one nonsilicone volatile oil;

3) a fatty phase consisting of a mixture of oils comprising at least one nonvolatile silicone oil, at least one volatile silicone oil and at least one volatile nonsilicone oil;

4) a fatty phase consisting of a mixture of oils comprising at least one volatile silicone oil, one nonvolatile nonsilicone oil and optionally at least one volatile nonsilicone oil; and 5) a fatty phase consisting solely of volatile silicone oil(s).

In cases 1), 2) and 3), the mixture may also comprise a nonvolatile nonsilicone oil. It being of course understood that in all cases, and in accordance with the invention, the fatty phase comprises a compound capable of reducing the temperature and the enthalpy of fusion of the structuring polymer.

Generally, the liquid fatty phase represents from 5 to 99% of the total weight of the composition and even better from 20 to 75%.

Structuring Silicone Polymer

The structuring polymer(s) of the composition are solid at room temperature (25° C.) and atmospheric pressure (760 mmHg) and are soluble in the liquid fatty phase at a temperature of 25 to 250° C.

The expression polymer is understood to mean, for the purpose of the invention, a compound having at least 2 repeating moieties, preferably at least 3 repeating moieties and even better 10 repeating moieties.

In the composition of the invention, the structuring silicone polymer generally represents from 0.5 to 80%, preferably from 2 to 60% and even better from 5 to 40% of the total weight of the composition.

Moreover, the polymer of the structuring polymer/oil(s), for example silicone oils and other oils, mass ratio is preferably from 0.1 to 50%.

The polymers used as structuring agents in the composition of the invention are polymers of the polyorganosiloxane type such as those described in the documents U.S. Pat. No. 5 874 069 [3], U.S. Pat. No. 5,919,441 [4], U.S. Pat. No. 6,051,216 [5] and U.S. Pat. No. 5,981,680 [11].

According to the invention, the polymers used as structuring agent may belong to the following two families:

1) polyorganosiloxanes comprising at least two groups capable of establishing hydrogen interactions, these two groups being situated in the polymer chain; and/or 2) polyorganosiloxanes comprising at least two groups capable of establishing hydrogen interactions, these two groups being situated on the grafts or branches.

The polymers comprising two groups capable of establishing hydrogen interactions in the polymer chain may be polymers comprising at least one moiety corresponding to the formula:

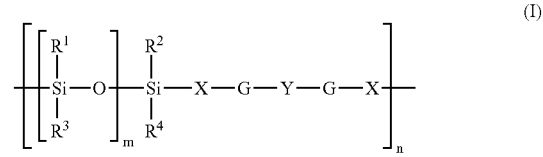

(I)

in which:

1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may possibly be linked to another chain of the polymer;

5) the groups G, which may be identical or different, represent divalent groups chosen from:

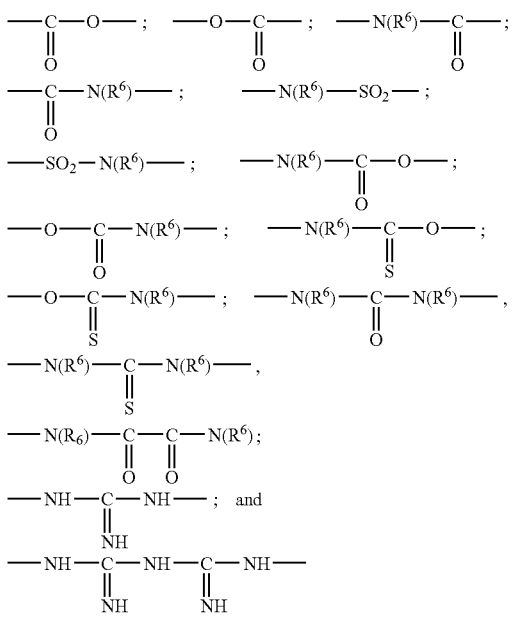

in which $R^6$ represents a hydrogen atom or a linear or branched $C_1$ to $C_{20}$ alkyl group, on condition that at least 50% of the groups $R^6$ of the polymer represent a hydrogen atom and that at least two of the groups G of the polymer are a group other than:

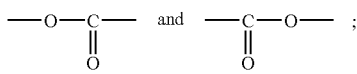

6) n is an integer ranging from 2 to 500 and preferably from 2 to 200, and m is an integer ranging from 1 to 1 000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

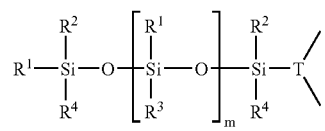

in which $R^1$, $R^2$, $R^3$, $R^4$, T and m are as defined above, and h) polyorganosiloxane chains of formula:

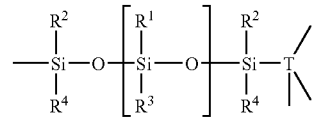

The polyorganosiloxanes of the second family may be polymers comprising at least one moiety corresponding to formula (II):

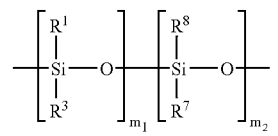

(II)

in which $R^1$ and $R^3$, which may be identical or different, are as defined above for formula (I), $R^7$ represents a group as defined above for $R^1$ and $R^3$, or represents the group of formula —X-G—$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents the group of formula —X-G—$R^9$ in which X, G and $R^9$ are as defined above, $m_1$ is an integer ranging from 1 to 998, and $m_2$ is an integer ranging from 2 to 500.

According to the invention, the polymer used as gelling agent may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea, urethane, thiourea, oxamido, guanidino and biguanidino groups, and combinations thereof.

These copolymers may be block copolymers or graft copolymers.

According to a first embodiment of the invention, the groups capable of establishing hydrogen interactions are amide groups of formulae —C(O)NH— and —HN—C(O)—.

In this case, the gelling agent may be a polymer comprising at least one moiety of formula (III) or (IV):

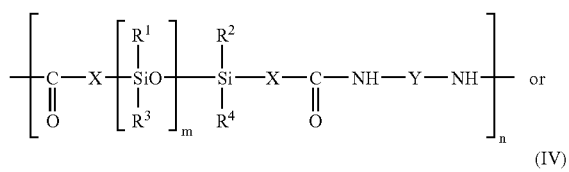

(III)

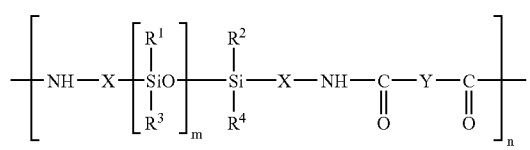

(IV)

in which $R^1$, $R^2$, $R^3$, $R^4$, X, Y, m and n are as defined above.

Such a moiety may be obtained:

either by a condensation reaction between a silicone containing α, ω-carboxylic acid ends and one or more diamines, according to the following reaction scheme:

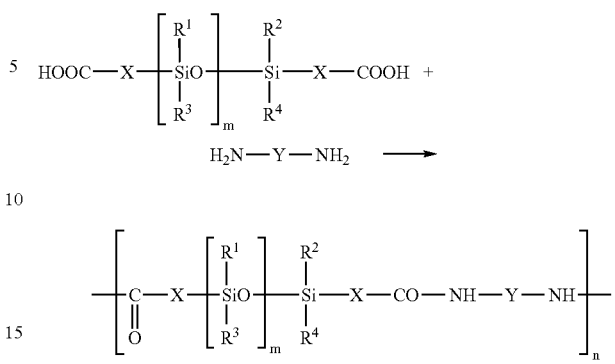

or by reaction of two molecules of α-unsaturated carboxylic acid with a diamine according to the following reaction scheme:

$CH_2=CH-X^1-COOH+H_2N-Y-NH_2 \rightarrow$ $CH_2=CH-X^1-CO-NH-Y-NH-CO-X^1-CH=CH_2$ followed by the addition of a siloxane to the ethylenic unsaturations, according to the following scheme:

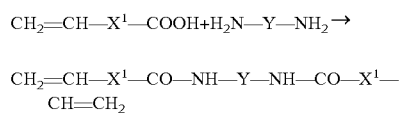

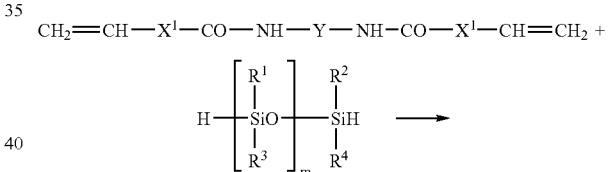

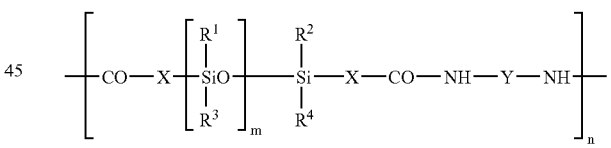

in which $X^1-(CH_2)_2$— corresponds to X defined above and Y, $R^1$, $R^2$, $R^3$, $R^4$ and m are as defined above;

or by reaction of a silicone containing α, ω-$NH_2$ ends and a diacid of formula HOOC—Y—COOH according to the following reaction scheme:

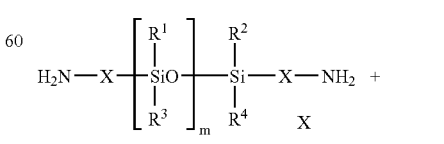

HOOC—Y—COOH  ⟶

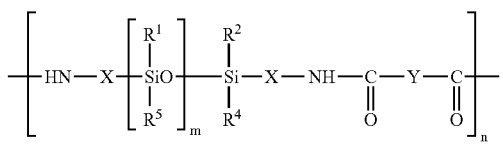

In these polyamides of formula (III) or (IV), m is preferably in the range from 1 to 700, more preferably from 15 to 500 and better still from 10 to 100, and n is in particular in the range from 1 to 500, preferably from 1 to 100 and better still from 4 to 25, X is preferably a linear or branched alkylene chain containing from 1 to 30 carbon atoms and in particular 1 to 20 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1) 1 to 5 amide, urea, urethane or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

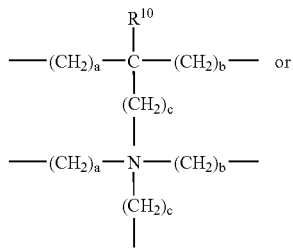

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

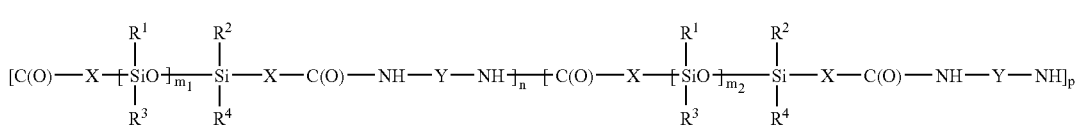

(V)

in which X, Y, n and $R^1$ to $R^4$ have the meanings given above, $m_1$ and $m_2$, which are different, are chosen in the range from 1 to 1 000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

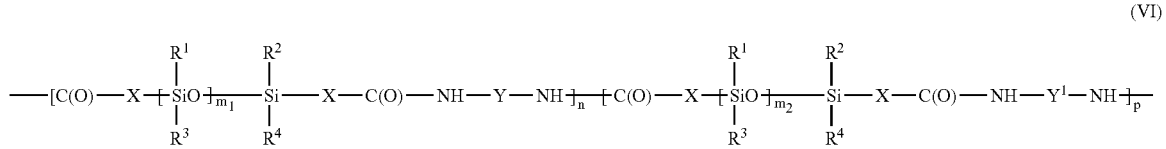

(VI)

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In this first embodiment of the invention, the structuring agent may also consist of a graft copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

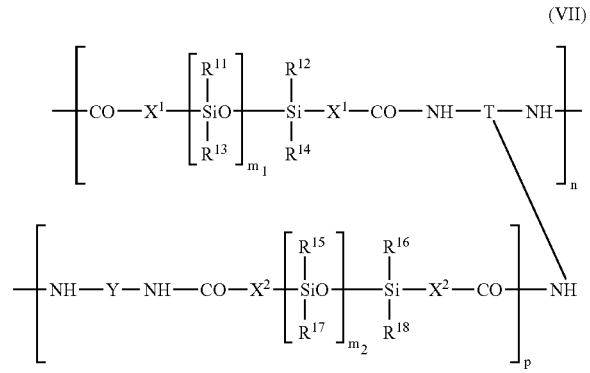

(VII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

In formula (VII), it is preferred that:

p is in the range from 1 to 25 and better still from 1 to 7,
$R^{11}$ to $R^{18}$ are methyl groups,
T corresponds to one of the following formulae:

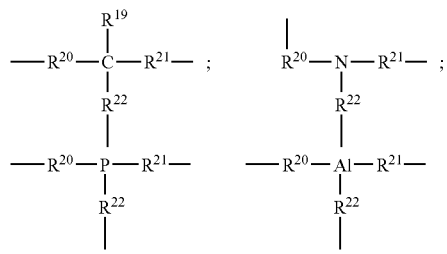

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

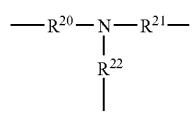

in particular with $R^{20}$, $R^{21}$ and $R^{22}$ representing —$CH_2$—$CH_2$—, $m_1$ and $m_2$ are in the range from 15 to 500 and better still from 15 to 45,
$X^1$ and $X^2$ represent —$(CH_2)_{10}$—, and
Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 50;
polyamides of formula (III) where m is from 30 to 500;
mixtures of two or more polyamides in which at least one polyamide has a value of m in the range from 15 to 50 and at least one polyamide has a value of m in the range from 30 to 50;
polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the portion corresponding to $m_2$ representing 1% to 99% by weight of the total weight of the polyamide;
mixtures of polyamide of formula (III) combining
1) 80% to 99% by weight of a polyamide in which n is equal to 2 to 10 and in particular 3 to 6, and
2) 1% to 20% of a polyamide in which n is in the range from 30 to 500 and in particular from 30 to 100;
mixtures of polyamide of formula (III) combining
1) 1% to 20% by weight of a polyamide where n is equal to 2 to 10, in particular 3 to 6, and
2) 80% to 99% of a polyamide where n is in the range from 30 to 500, in particular from 30 to 100;
polyamides corresponding to formula (VI) in which at least one of the groups Y and $Y^1$ contains at least one hydroxyl substituent;
polyamides of formula (III) synthesized with at least one portion of an activated diacid (diacid chloride, dianhydride or diester) instead of the diacid;
polyamides of formula (III) in which X represents —$(CH_2)_3$— or —$(CH_2)_{10}$; and
polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the ends of the polymer chains may end with:

a $C_1$ to $C_{50}$ alkyl ester group by introducing a $C_1$ to $C_{50}$ monoalcohol during the synthesis,
a $C_1$ to $C_{50}$ alkylamide group by taking as stopping group a monoacid if the silicone is α, ω-diaminated, or a monoamine if the silicone is an α, ω-dicarboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based structuring agents containing silicones may be produced by silylic amidation of polyamides based on fatty acid dimer. This approach involves the reaction of free acid sites existing on a polyamide as end sites, with oligosiloxane-monoamines and/or oligosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and, the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a structuring agent based on a copolymer between a hydrocarbon-based polyamide and a silicone polyamide, by transamidation of a polyamide having, for example, an ethylenediamine constituent, with an oligosiloxane-α, ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a graft copolymer comprising a hydrocarbon-based polyamide backbone with pendent oligosiloxane groups.

This may be obtained, for example:
by hydrosilylation of unsaturated bonds in polyamides based on fatty acid dimers;
by silylation of the amide groups of a polyamide; or
by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to a second embodiment of the invention, the structuring agent consists of a homopolymer or a copolymer comprising urethane or urea groups.

As previously, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

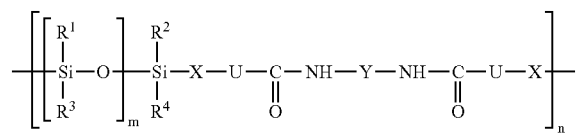

(VIII)

in which $R^1$, $R^2$, $R^3$, $R^4$, X, Y, m and n have the meanings given above for formula (I), and U represents —O— or —NH—, such that:

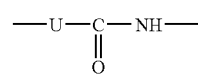

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

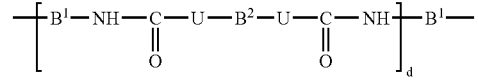

(IX)

in which $B^1$ is a group chosen from the groups given above for Y, U is —O— or —NH— and $B^2$ is chosen from:
linear or branched $C_1$ to $C_{40}$ alkylene groups,
$C_5$ to $C_{12}$ cycloalkylene groups, optionally-bearing alkyl substituents, for example one to three methyl or ethyl groups, or alkylene substituents, for example the diol radical: cyclohexanedimethanol,
phenylene groups that may optionally bear $C_1$ to $C_3$ alkyl substituents, and groups of formula:

in which T is a hydrocarbon-based trivalent radical possibly containing one or more heteroatoms such as oxygen, sulphur and nitrogen and $R^5$ is a polyorganosiloxane chain or a linear or branched $C_1$ to $C_{50}$ alkyl chain.

T can represent, for example:

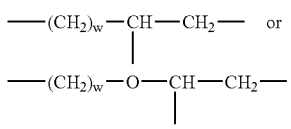

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or the group:

with $R^5$ being a polyorganosiloxane chain.

As previously, the polymer constituting the structuring agent may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

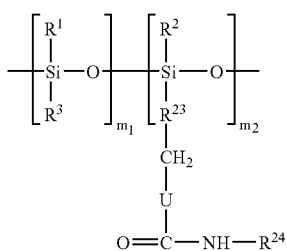

(X)

in which $R^1$, $R^2$, $R^3$, $m_1$ and $m_2$ have the meanings given above for formula (I), U represents O or NH, R represents a $C_1$ to $C_{40}$ alkylene group, optionally comprising one or more heteroatoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as structuring agents in the compositions of the invention.

The siloxane polymers may have a single urea or urethane group per branch or may have branches containing two urea or urethane groups, or alternatively they may contain a mixture of branches containing one urea or urethane group and branches containing two urea or urethane groups.

They may be obtained from branched polysiloxanes, comprising one or two amino groups per branch, by reacting these polysiloxanes with monoisocyanates.

As examples of starting polymers of this type containing amino and diamino branches, mention may be made of the polymers corresponding to the following formulae:

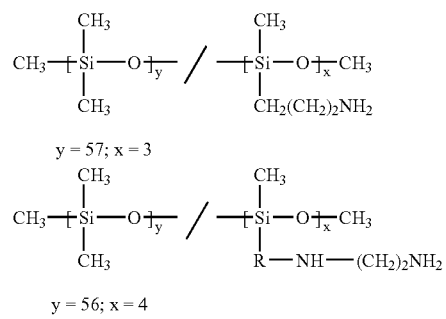

y = 57; x = 3 y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form the groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane moieties and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

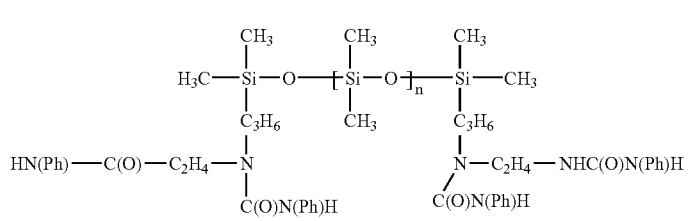

(XI)

(Ph = phenyl)

in which Ph is a phenyl group and n is a number from 0 to 300, in particular from 0 to 100, for example 50.

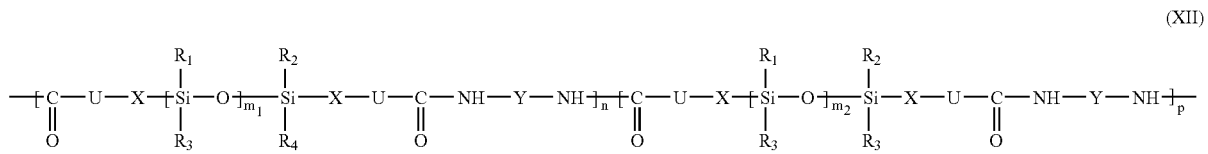

(XII)

This polymer is obtained by reacting the following polysiloxane containing amino groups:

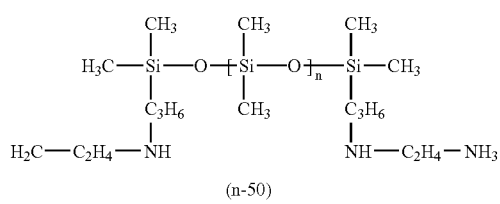

(n-50)

with phenyl isocyanate.

The polymers of formula (VIII) comprising urea or urethane groups in the chain of the silicone polymer may be obtained by reaction between a silicone containing α, ω-NH$_2$ or —OH end groups, of formula:

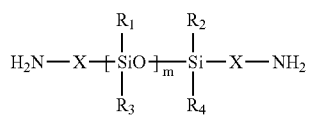

in which m, $R^1$, $R^2$, $R^3$, $R^4$ and X are as defined for formula (I), and a diisocyanate OCN—Y—NCO in which Y has the meaning given in formula (I); and optionally a diol or diamine coupling agent of formula H$_2$N—B$^2$—NH$_2$ or HO—B$^2$—OH, in which B$^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone moieties. In this case, the copolymer may correspond, for example, to the formula:

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

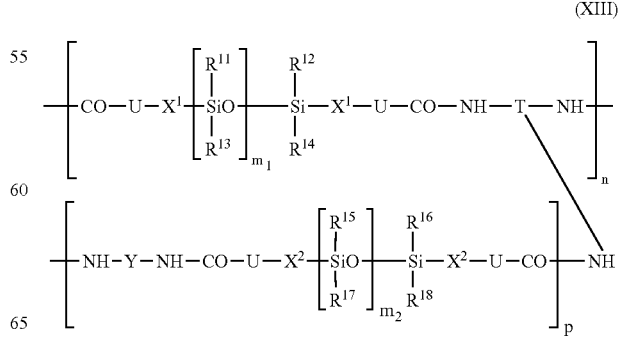

A polyurethane or polyurea silicone containing branches comprising an organosiloxane chain with groups capable of establishing hydrogen interactions is thus obtained. Such a polymer comprises, for example, a moiety corresponding to the formula:

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

As in the case of the polyamides, this copolymer can also comprise polyurethane silicone moieties without branching.

In this second embodiment of the invention, the siloxane-based polyureas and polyurethanes that are preferred are:

polymers of formula (VIII) in which m is from 15 to 50;
polymers of formula (VIII) in which m is from 30 to 500;
mixtures of two or more polymers in which at least one polymer has a value of m in the range from 15 to 50 and at least one polymer has a value of m in the range from 30 to 50;
polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;
mixtures of polymer of formula (VIII) combining
1) 1% to 20% by weight of a polymer where n is equal to 2 to 10, in particular 3 to 6, and
2) 80% to 99% of a polymer where n is in the range from 30 to 500, in particular from 30 to 100,
copolymers comprising two moieties of formula (VIII) in which at least one of the groups Y contains at least one hydroxyl substituent;
polymers of formula (VIII) synthesized with at least one portion of an activated diacid (diacid chloride, dianhydride or diester) instead of the diacid;
polymers of formula (VIII) in which X represents —(CH₂)₃— or —(CH₂)₁₀—; and
polymers of formula (VIII) in which the polymers end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α, ω-difunctional block of non-silicone nature, for example a polyester, a polyether or a polyolefin.

As has been seen previously, gelling agents consisting of homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

(1)

(2)

(3)

(4)

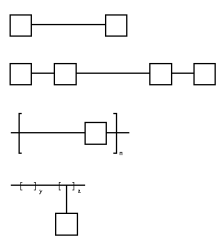

-continued

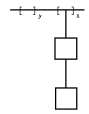

(5)

in which the continuous line is the main chain of the siloxane polymer and the squares represent the groups capable of establishing hydrogen interactions.

In case (1), the groups capable of establishing hydrogen interactions are arranged at the ends of the main chain. In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

According to the invention, the structuring of the liquid fatty phase containing at least one silicone oil, is obtained with the aid of one or more of the polymers mentioned above, in combination with one or more compounds capable of reducing the melting temperature and the enthalpy of fusion of this or these polymers.

As examples of polymers that may be used, mention may be made of the silicone polyamides obtained in accordance with Examples 1 to 3 of document U.S. Pat. No. 5,981,680.

The polymers and copolymers used in the composition of the invention advantageously have a softening point from 65° C. to 190° C. Preferably, they have a softening point ranging from 70 to 130° C. and better still from 80° C. to 105° C. This softening point is lower than that of the known structuring polymers, which facilitates the use of the polymers, allows the use of volatile oils and limits the deteriorations of the liquid fatty phase.

They have good solubility in silicone oils and produce macroscopically homogeneous compositions. Preferably, they have an average molecular mass from 500 to 200 000, for example from 1 000 to 100 000, preferably from 2 000 to 200 000.

Compound Capable of Reducing the Enthalpy of Fusion and Possibly the Melting Temperature of the Structuring Polymer The compound according to the invention contains one or more compounds capable of lowering, reducing or decreasing the enthalpy of fusion (ΔH) and possibly the melting temperature (m.p.) of the structuring polymer; preferably capable of lowering the enthalpy of fusion (ΔH) and the melting temperature (m.p.). This or these compounds make it possible to facilitate the application of the compositions and to improve the deposit obtained with these compositions, that is to say that this deposit is a larger mass than that obtained under the same conditions with compositions not containing these compounds. The said compound(s) are capable of lowering, decreasing or reducing the enthalpy of fusion and possibly the melting temperature of the structuring polymer(s) of the fatty phase.

The expression lowering of the enthalpy of fusion is understood to mean that the polymer, once it has been brought into contact with this or these compounds, has an enthalpy, expressed relative to the mass of the polymer present, less than that which it exhibits in the pure state.

The enthalpy of fusion is measured using differential scanning calorimetry, for example the calorimeter sold under the name MDSC 2920 by the company TA Inst., by the so-called power compensating calorimetric analysis technique (Differential Scanning Calorimetry), in which a temperature rise of 2° C. per minute is applied.

The enthalpy of fusion corresponds to the surface under the curve of the thermogram obtained.

The thermogram is the power compensating differential calorimetric enthalpy curve: this curve represents the quantity of heat provided by a unit of time plotted on the y-axis, as a function of the temperature on the x-axis.

The lowering of the enthalpy of fusion $\Delta H$ depends on the quantity of compound(s) above, in the composition. This quantity is such that it is sufficient to cause a decrease in the enthalpy of fusion $\Delta H$, this decrease is generally at least 3 J/g of pure polymer, preferably at least 4 J/g of pure polymer, preferably still 5 to 10 J/g.

When the compound(s) are included in such quantities, all the effects described above are observed. In other words, the incorporation of these compounds, which are potentially capable of causing a decrease in the enthalpy of fusion, in a sufficient quantity, effectively allows them to exert this initially only potential effect.

In addition, the said compound(s) are generally also capable of lowering the melting temperature (m.p.) of the structuring polymer.

The expression lowering of the melting temperature, of the melting point, is understood to mean that the polymer, once it has been brought into contact with this or these compounds, has a melting temperature less than that which it exhibits in the pure state.

The melting temperature, the melting point, correspond, according to the invention, to the melting point which is measured using differential scanning calorimetry, for example the calorimeter sold under the name MDSC 2920 by the company TA Inst., by the so-called power compensating calorimetric analysis technique (Differential Scanning Calorimetry), in which a temperature rise of 2° C. per minute is applied. The melting point considered is the point corresponding to the temperature of the most endothermic peak of the thermogram obtained. The thermogram was defined above.

To evaluate the lowering of the melting temperature caused by the compounds capable of lowering the melting point included in the composition of the invention, the melting temperature of the pure polymer is first measured by the above method, and then the polymer is solubilized beyond its m.p. previously determined, with one or more compounds capable of lowering or decreasing the melting temperature and the melting point is measured by the same method, under the same conditions, on the mixture of the polymer and of the compound(s).

The lowering of the melting temperature depends on the quantity of compound(s) above in the composition. This quantity should be such that it is sufficient to cause a real decrease in, or lowering of the melting temperature of the polymer(s). This decrease or this lowering is generally at least 3° C., preferably at least 4° C., preferably still from 5 to 20° C.

In addition, the compound(s) capable of lowering the melting temperature and the enthalpy of fusion are advantageously compounds which lead to compositions which are macroscopically homogeneous and/or which are soluble or dispersible in the fatty phase of the composition.

A macroscopically homogeneous composition is a composition for which a single phase is observed with the naked eye, at room temperature (between 20 and 25° C.).

The compound capable of lowering the enthalpy of fusion of the structuring polymer is preferably soluble in the fatty phase of the composition, that is to say that the compound is in the form of individualized molecules distributed in the fatty phase.

The compound capable of lowering the enthalpy of fusion of the structuring polymer is advantageously dispersible in the fatty phase of the composition, that is to say that the compound is in the form of lumps of molecules, having a size which is not detectable with the naked eye, homogeneously distributed in the fatty phase.

These properties may be described by the fact that these compounds are "compatible" with the structuring polymer and optionally with the other components of the composition.

Preferably, the compounds capable of lowering the enthalpy of fusion of the polymer also lower the melting temperature.

Preferably still, these compounds lower the melting temperature and lead to macroscopically homogeneous compositions.

In other words, preferably, the particular compounds used in the composition of the invention should simultaneously satisfy the three conditions listed above and relating to the lowering of the melting temperature, to the lowering of the enthalpy of fusion and to the formation of macroscopically homogeneous compositions.

The compounds capable of causing a reduction in the enthalpy of fusion and optionally in the melting temperature of the structuring polymer is (are) chosen from hydrocarbon and/or silicone compounds comprising at least one functional group comprising a free electron doublet capable of interacting with the hydrogen bonds of the polymer. This functional group is chosen, for example, from hydroxyl (alcohol), carboxyl, amino, primary, secondary and tertiary amines, urea and urethane, ether and ester.

The preferred functional group is the alcohol functional group and as a result, the compounds capable of causing a decrease in the enthalpy of fusion and optionally in the melting temperature of the structuring polymer are preferably chosen from monoalcohols, polyols such as diols and triols and the like, and polyol ethers.

In particular, the compound(s) capable of causing a decrease in the enthalpy of fusion and optionally in the melting temperature may be chosen from silicone diols.

Suitable silicone diols are described in particular in the document U.S. Pat. No. 5,969,172, to the description of which reference may be made, and are marketed by the company GENERAL ELECTRIC.

The compounds of this document correspond to the following formula:

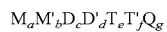

where the subscripts a, c, d, e, f and g are zero or a positive integer, provided that the sum of the subscripts b, d and f is one or higher;

where M has the formula:

where each R' independently represents a monovalent hydrocarbon radical having from 1 to 40 carbon atoms;

M' has the formula:

$$R_{3-h}^{II}R_h^{III}SiO_{1/2}$$

where each $R^{II}$ is independently a monodivalent hydrocarbon radical having from 1 to 40 carbon atoms, $R^{III}$ is a monovalent hydrocarbon radical chosen from the group consisting of $H_2(OH)CCH(OH)CH_2OCH_2CH_2CH_2$— and $(HOCH_2)_2C(CH_2CH_3)CH_2OCH_2CH_2CH_2$— the subscript h is 1, 2 or 3;

D has the formula:

$$R_2^{IV}SiO_{2/2}$$

where each $R^{IV}$ is independently a monovalent hydrocarbon radical having from 1 to 40 carbon atoms;

D' has the formula:

$$R_{2-i}^{V}R_i^{VI}SiO_{2/2}$$

where each $R^{IV}$ is independently a monovalent hydrocarbon radical having from 1 to 40 carbon atoms, $R^{V}$ is a monovalent hydrocarbon radical chosen from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2;

T has the formula:

$$R^{VII}SiO_{3/2}$$

where each $R^{VII}$ is independently a monovalent hydrocarbon radical having from 1 to 40 carbon atoms, T' has the formula:

$$R^{VIII}SiO_{3/2}$$

where $R^{VIII}$ is a monovalent hydrocarbon radical chosen from the group-consisting of $H_2$ (OH)CCH(OH) $CH_2OCH_2CH_2CH_2$— and $(HOCH_2)_2C$ $(CH_2CH_3)$ $CH_2OCH_2CH_2CH_2$— and Q has the formula $SiO_{4/2}$.

The preferred compounds are the compounds indicated in the following Table 3:

TABLE 3

| Compound | Structure | Functional group |
|---|---|---|
| 1 | MD$_4$'M | 1,3-DIOL |
| 2 | M' D$_3$M' | 1,3-DIOL |
| 3 | MD$_{6.4}$D'$_5$M | 1,3-DIOL |
| 4 | MD$_{10}$D'$_7$M | 1,3-DIOL |
| 5 | M' D$_3$M' | 1,2-DIOL |
| 6 | M' D$_5$M' | 1,3-DIOL |
| 7 | MD$_{6.4}$D'$_5$M | 1,2-DIOL |
| 8 | MD$_3$D'$_3$M | 1,2-DIOL |
| 9 | MD$_7$D'$_3$M | 1,3-DIOL |
| 10 | M' D$_5$M' | 1,2-DIOL |
| 11 | M' D$_{7.5}$M' | 1,3-DIOL |
| 12 | MD$_7$D'$_3$M | 1,2-DIOL |
| 13 | M' D$_{7.5}$M' | 1,2-DIOL |
| 14 | M' D$_{10}$M' | 1,3-DIOL |
| 15 | M' D$_{10}$M' | 1,2-DIOL |
| 16 | MD$_{20}$D'$_3$M | 1,3-DIOL |
| 17 | M' D$_{25}$M' | 1,2-DIOL |

In Table 3: 1,3-DIOL means that the functional group, that is to say $R^{III}$, $R^{V}$ or $R^{VIII}$ is a group $(HOCH_2)_2C(CH_2CH_3)$ $CH_2OCH_2CH_2CH_2$— namely a group derived from the monoallyl ether of trimethylolpropane (TMPMAE), and 1,2-DIOL means that the functional group is a group $H_2(OH)$ $CCH(OH)CH_2OCH_2CH_2CH_2$—, namely a group derived from monoallylglycerine.

In Table 3, the compounds further preferred are M'D$_3$M', M'D$_{7.5}$M', M'D$_{10}$M' and M'D$_{25}$M'.

The compounds capable of causing a decrease in the enthalpy of fusion and optionally in the melting temperature may also be chosen from compounds of the oxyalkylenated polydi(alkyl)siloxane type, in which the alkyl groups of the siloxane have from 1 to 4 carbon atoms and the alkylene group has from 1 to 4 carbon atoms, preferably the alkyl groups of polydi(alkyl)siloxane are methyl groups and the oxyalkylene groups are oxypropylene and/or oxyethylene groups and the compounds are PDMS oxypropylene and/or oxyethylene.

Compounds of this type are known by the name dimethicone polyol or copolyol (PDMS-EO-PO) among which there may be mentioned polydimethylsiloxane oxyethylene (7/9 EO) oxypropylene (10/14 PO) from DEGUSSA, marketed under the reference ABIL B 8873, or polydimethylsiloxane oxyethylene (200 E) oxypropylene (200 P) known under the INCI name PEG/PPG-17/18 dimethicone and marketed by DOW CORNING under the name "Q2-5220 RESIN modifier".

Other compounds capable of causing a decrease in the enthalpy of fusion and optionally the melting temperature of the polymer are monoalkyl ethers of polyalkylene (1-4 carbon atoms) glycols, for example monoalkyl ethers of polypropylene glycol or of polyalkylene glycol, such as the monomyristyl ether of polypropylene glycol of formula:

$$H—[OCH(CH_3)CH_2]_nO—(CH_2)_{13}—CH_3$$

with n=2 to 200.

Another family of compounds capable of causing a decrease in the enthalpy of fusion and possibly the melting temperature of the structuring polymer are the linear or branched aliphatic monoalcohols having more than 8 carbon atoms, for example from 12 to 26 carbon atoms such as 2-butyloctanol, 2-hexyldecanol, 2-undecyldecanol, 2-undecylpentadecanol, oleyl alcohol, a preferred alcohol being octyldodecanol.

It is possible to include a single compound capable of reducing the enthalpy of fusion and possibly the melting temperature of the polymer or of the polymers or alternatively several of these compounds which may each be chosen from any of the groups and families of compounds defined above.

The content of compound or of compound(s) capable of lowering the enthalpy of fusion and possibly the melting temperature of the polymer(s) is generally from 5 to 25% by weight, preferably from 10 to 20% by weight.

This quantity is the sufficient quantity defined above and which makes it possible to obtain a decrease in the enthalpy of fusion of the polymer and possibly in the melting temperature of the polymer generally of at least 3 J/g and of at least 3° C. respectively.

The use of compounds reducing the enthalpy of fusion and possibly the melting temperature of the polymers, such as PASi's, in cosmetic compositions is not known in the art. The combination of such compounds with the particular polymers according to the invention is neither described nor suggested in the prior art. Nothing made it possible to think, in the light of the prior art, that such a combination could lead to a surprising improvement in the properties, in particular in the ease of application and possibly the gloss of a cosmetic composition comprising this combination, as well as an improvement in the properties, in particular in the mass and possibly the gloss of a deposit obtained from a cosmetic composition comprising this combination.

The quantities of the compound(s) lowering the enthalpy of fusion and possibly the melting temperature of the polymer(s), and the structuring polymer(s) may be chosen according to the desired hardness and the desired stability of the compositions and according to the specific application envisaged. The respective quantities of the (at least one) structuring polymer and of the compound(s) lowering the enthalpy of fusion and possibly the melting point may be such that a disintegratable solid which does not run under the effect of its own weight is obtained.

According to one of the embodiments of the invention, which corresponds to a stick, the composition preferably has a hardness ranging from 20 to 2 000 gf and better still from 20 to 900 gf, particularly from 20 to 600 gf, and for example from 150 to 450 gf. This hardness may be measured according to a method of penetration of a probe into the said composition and in particular with the aid of a texture analyser (for example TA-TXT2i from Rheo) equipped with an ebonite cylinder 25 mm in height and 8 mm in diameter. The hardness measurement is carried out at 20° C. at the centre of five samples of the said composition. The cylinder is introduced into each sample of composition at a pre-speed of 2 mm/s, then at a speed of 0.5 mm/s and finally at a post-speed of 2 mm/s, the total displacement being 1 mm. The recorded hardness value is that of the maximum peak. The measurement error is ±50 gf.

The hardness may also be measured by the "cheese wire" method, which consists in cutting a tube of lipstick 12.7 mm in diameter and in measuring the hardness at 20° C., using a DFGHS 2 tensile testing machine from the company Indelco-Chatillon, travelling at a speed of 100 mm/minute. It is expressed as the shear force (expressed in gram-force) required to cut a stick under these conditions. According to this method, the hardness of a composition in stick form according to the invention ranges from 30 to 300 gf, preferably from 30 to 250 gf and for example from 30 to 200 gf, even better from 30 to 120 gf, when the diameter of the stick is equal to 12.7 mm.

The hardness of the composition may moreover be lower as long as the composition is self-supporting and can disintegrate easily to form a satisfactory deposit on the skin and the lips. By virtue of the presence in the composition of the invention of a compound capable of lowering the enthalpy of fusion and possibly the temperature of the polymer, an easy application and a satisfactory deposit in sufficient quantities are obtained in all cases.

In addition, with these hardness values, the composition of the invention shows good impact strength.

Generally, the silicone polymer/compound capable of lowering the enthalpy of fusion and possibly the melting temperature of the polymer mass ratio is generally in the range from 0.1 to 50, preferably from 0.5 to 25 and even better from 1 to 15.

The structuring silicone polymer preferably represents 5 to 30% by weight of the composition.

Other Additives

The composition of the invention may also comprise any ingredient usually used in the field under consideration, and especially those chosen from fillers, dyes that are soluble in polyols or in the fatty phase, antioxidants, essential oils, preserving agents, perfumes, liposoluble polymers, especially hydrocarbon-based liposoluble polymers such as polyalkylenes or polyvinyl laurate, liquid-fatty-phase structuring agents, waxes, gums, resins, surfactants, for instance trioleyl phosphate, additional cosmetic or dermatological active agents such as, for example, water, emollients, moisturizers, vitamins, liquid lanolin, essential fatty acids, lipophilic sunscreens or sunscreens that are soluble in polyols, and mixtures thereof. The composition according to the invention may also contain lipid vesicles of ionic and/or non-ionic type. These ingredients, besides the water, may be present in the composition in the usual manner in a proportion of from 0% to 20%, preferably from 0.01% to 20%, of the total weight of the composition and better still from 0.1% to 10%.

In the case where the composition contains an aqueous phase, which is the case for a simple or multiple emulsion, this aqueous phase can represent 0.1% to 70% of the total weight of the composition, especially from 0.5% to 40% and better still from 1% to 20%. This aqueous phase can contain any water-miscible compound such as polyols and may be optionally gelled with a suitable gelling agent.

Needless to say, the person skilled in the art will take care to select the optional additional ingredients and/or the amount thereof such that the advantageous properties of the composition according to the invention are not, or are not substantially, adversely affected by the envisaged addition.

The compositions of the invention may in particular contain one or more waxes, for example polyethylene wax, but the use of wax is avoided if it is desired to obtain glossy, or even transparent products. Generally, the amount of wax does not exceed 20% and preferably 10%; it represents, for example, from 3% to 5% of the total weight of the composition. Even in the absence of waxes or in the presence of a small quantity of waxes, the compositions according to the invention all exhibit the advantageous properties listed above.

The composition according to the invention may be in the form of an optionally tinted care composition for keratinous materials such as the skin, the lips and/or the superficial body growths, in the form of a sun protection or care composition, especially in the form of a make-up-removing product, in the form of a stick or a dome, or in cast form. It can especially be used as a care base for the skin, the superficial body growths or the lips (lip balms, for protecting the lips against the cold and/or sunlight and/or the wind, or a care cream for the skin, the nails or the hair).

The composition of the invention may be provided in particular in the form of a soft, transparent gel, or of a transparent stick.

The composition of the invention may also be in the form of a foundation, optionally having care or treatment properties, a blusher, a face powder, an eyeshadow, a concealer product, an eyeliner or a make-up product for the body; a lip make-up, for instance a lipstick, a lip gloss or a pencil, optionally having care or treatment properties; a make-up for the superficial body growths, for instance the nails or the eyelashes, in particular in the form of a mascara cake, or for the eyebrows and the hair, especially in the form of a pencil.

In particular, the composition of the invention may be a cosmetic product containing cosmetic active agents, for instance essential oils, vitamins, moisturizers, sunscreens and ceramides.

In the case of make-up compositions, hydrophobic or hydrophilic solid particles may constitute the pigment(s) for making up the skin, the lips and/or the superficial body growths.

Needless to say, the composition of the invention must be cosmetically or dermatologically acceptable, that is to say that it must contain a non-toxic physiologically acceptable medium that can be applied to the skin, the superficial body growths or the lips of human beings. For the purposes of the invention, the expression "cosmetically acceptable" means a composition of pleasant appearance, odour and feel.

Moreover, the make-up or care compositions in accordance with the invention must comprise at least 10% by mass of a non-volatile oil (silicone oil or non-silicone oil) and/or of a pasty or viscous product in order to obtain a product which is comfortable and which does not cause tightness.

The expression pasty product is understood to mean a viscous fatty substance containing a liquid fraction and a solid fraction. For the purposes of the invention, the expression "pasty fatty substances" means fatty substances with a melting point ranging from 20 to 55° C. and preferably 25 to 45° C., and/or a viscosity at 40° C. ranging from 0.1 to 40 Pa·s (1 to 400 poises) and preferably 0.5 to 25 Pa·s measured using a Contraves TV or Rheomat 180 viscometer, equipped with a spindle rotating at 240 min$^{-1}$ for a power supply at 60 Hz or at 200 min$^{-1}$ for a power supply at 50 Hz or alternatively measured in the newtonian domain of a flow observed on a Haake Rs75 rheometer in a flat cone spindle at 40° C.

A person skilled in the art can select the spindle for measuring the viscosity, on the basis of his general knowledge, so as to be able to measure the viscosity of the tested pasty compound.

The melting point values correspond, according to the invention and as already indicated above, to the most endothermic melting peak measured by the "Differential Scanning Calorimetry" method with a temperature rise of 20° C./min.

By way of example of pasty products that may be used in the invention, mention may be made of lanolins and lanolin derivatives, for instance acetylated lanolins or oxypropylenated lanolins or isopropyl lanolate, with a viscosity of 18 to 21 Pa·s and preferably 19 to 20.5 Pa·s, and/or a melting point of 30 to 55° C., preferably 30 to 40° C., and mixtures thereof. Esters of fatty acids or of fatty alcohols may also be used, especially those containing 20 to 65 carbon atoms (melting point of about 20 to 35° C. and/or viscosity at 40° C. ranging from 0.1 to 40 Pa·s), for instance triisostearyl citrate or cetyl citrate; arachidyl propionate; polyvinyl laurate; cholesterol esters, for instance triglycerides of plant origin such as hydrogenated plant oils, viscous polyesters, for instance poly(12-hydroxystearic acid) and mixtures thereof. Triglycerides of plant origin that may be used include hydrogenated castor oil derivatives, such as "THIXINR" from Rheox.

Mention may also be made of silicone-based pasty fatty substances such as polydimethylsiloxanes (PDMSs) containing pendent chains of the alkyl or alkoxy type containing from 8 to 24 carbon atoms, and having a melting point of 20-55° C., for example 20 to 40° C., for instance stearyl dimethicones, especially those sold by the company Dow Corning under the trade names DC2503 and DC25514, and mixtures thereof.

The pasty fatty substance(s) may be present in a proportion of from 0 to 60% by weight relative to the total weight of the composition, preferably in a proportion of 0.1-45% by weight and even more preferably in a proportion of 2-30% by weight.

According to the invention, the composition generally comprises, in addition, solid particles chosen from fillers and pigments (including pearlescent pigments) and mixtures thereof.

The expression pigments is understood to mean any solid particle insoluble in the composition which serves to give and/or modify a colour and/or an iridescent appearance.

The pigments may be white or coloured, inorganic and/or organic, coated or not. The inorganic pigments may be chosen for example from zinc oxides, iron oxides, titanium oxides and mixtures thereof. There may thus be mentioned, among the inorganic pigments, titanium or zinc dioxide, optionally surface-treated, zirconium or cerium oxides, and iron or chromium oxides, manganese violet, ultramarine blue, chromium hydrate and ferric blue. Among the organic pigments, there may be mentioned carbon black, pigments of the D & C type, and lacquers based on carmine, barium, strontium, calcium or aluminium. The pigments may represent from 0.1 to 50%, preferably from 0.5 to 40%, and even better from 2 to 30% of the total weight of the composition.

According to the invention, the composition may furthermore contain colouring matter which may be chosen from lipophilic dyes, hydrophilic dyes, and mixtures thereof.

This colouring matter is generally present in an amount of 0.01 to 50% of the total weight of the composition; preferably 5 to 30%, if it is present. It should be noted that a colouring effect may also be provided by the pigments (and pearlescent pigments) already described above in the context of solid particles.

The liposoluble dyes are, for example, Sudan red, DC Red 17, DC Green 6, β-carotene, soybean oil, Sudan brown, DC Yellow 11, DC Violet 2, DC Orange 5, quinoline yellow and annatto.

The hydrophilic dyes are in particular beet juice and methylene blue. Soluble dyes can represent from 0% to 20% of the weight of the composition and better still from 0.1% to 6% (if present).

The composition according to the invention may be manufactured by known methods, generally used in the cosmetic or dermatological field. It may be manufactured by the method which consists in heating, the polymer at least to its softening point, adding thereto the optional waxes and/or pasty compounds, the oil(s), the compound(s) lower the enthalpy of fusion and possibly the melting temperature of the polymer, and then in mixing the whole until a clear solution is obtained. The colouring matter and/or the solid particles and the additives are then added, with stirring. The homogeneous mixture obtained can then be cast in a suitable mould such as a lipstick mould, or directly into the packaging articles, especially a case or dish.

The subject of the invention is also a make-up structured solid composition for the skin, the lips and/or the superficial body growths, containing at least one pigment in a sufficient quantity for applying make-up to the skin, the lips and/or the superficial body growths and a liquid continuous fatty phase structured with at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., the said-liquid fatty phase comprising at least one compound capable of lowering the enthalpy of fusion and possibly the melting temperature of the structuring polymer, the said composition being optionally provided in the form of a solid, and the pigment, the liquid fatty phase, the compound capable of lowering the enthalpy of fusion and possibly the melting temperature of the structuring polymer and the structuring polymer forming a physiologically acceptable medium.

This make-up composition is preferably self-supporting.

The subject of the invention is also a lipstick structured composition, containing at least one pigment in a sufficient quantity for applying make-up to the lips and a liquid continuous fatty phase structured with at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., the liquid fatty phase comprising at least one compound capable of lowering the enthalpy of fusion and possibly the melting temperature of the structuring polymer, and the pigment, the fatty phase, the polymer, and the compound capable of lowering the enthalpy of fusion and possibly the melting temperature of the structuring polymer forming a physiologically acceptable medium.

The invention relates to a cosmetic care, make-up or treatment method for the keratinous materials of human beings, comprising the application to the keratinous materials of a cosmetic composition in accordance with the invention.

The subject of the invention is also the use, in a cosmetic composition or for the manufacture of a physiologically acceptable composition, containing a continuous liquid fatty phase, of a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., the liquid fatty phase optionally consisting partially or totally of silicone oil(s) having a flash point equal to or greater than 40° C. and comprising one compound at least capable of lowering the enthalpy of fusion and possibly the melting temperature of the structuring polymer, the said composition being provided in the form of a self-supporting solid with a hardness ranging from 20 to 2 000 gf and preferably from 20 to 900 gf and even better from 20 to 600 gf.

The subject of invention is also the use of a continuous liquid fatty phase essentially structured with a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., the liquid fatty phase optionally consisting partially or totally of volatile oil(s) having a flash point equal to or greater than 40° C. and comprising at least one compound capable of lowering the enthalpy of fusion and possibly the melting temperature of the polymer, in a cosmetic composition or for the manufacture of a physiologically acceptable composition which is easy to apply and/or gives a deposit with a large mass.

The subject of the invention is also the use of a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, urethane, thiourea, oxamido, guanidino and biguanidino groups, the polymer being solid at room temperature and soluble in the liquid fatty phase at a temperature of 25 to 250° C., in a cosmetic composition or for the manufacture of a physiologically acceptable composition, containing a liquid continuous fatty phase and at least one compound capable of lowering the enthalpy of fusion and possibly the melting temperature of the polymer, to structure the said composition in the form of a self-supporting solid.

The subject of the invention is also the use of the combination of a continuous liquid fatty phase essentially structured with a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in a chain of the moiety or in the form of a graft, and at least two groups capable of establishing hydrogen interactions chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., the liquid fatty phase optionally consisting partially or totally of volatile oil(s) having a flash point equal to or greater than 40° C. and comprising at least one compound capable of lowering the enthalpy of fusion and possibly the melting temperature of the polymer, in a cosmetic composition or for the manufacture of a physiologically acceptable composition, as agent for facilitating the application of the said composition, and/or optionally increasing its gloss and the gloss of a deposit of the said composition.

The invention additionally relates to the use of a continuous liquid fatty phase, optionally structured with a sufficient quantity of at least one structuring polymer (homopolymer or copolymer) having a weight-average molecular mass ranging from 500 to 500 000, containing at least one moiety comprising:

at least one polyorganosiloxane group consisting of 1 to 1000 organosiloxane units in a chain of the moiety or in the form of a graft, and at least two groups capable of establishing hydrogen interactions, chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., the liquid fatty phase optionally partially or totally consisting of volatile oil(s) and comprising at least one compound capable of lowering the enthalpy of fusion and possibly the melting temperature of the polymer, in a cosmetic composition or for the manufacture of a physiologically acceptable composition as an agent for increasing the mass of a deposit of the said composition.

According to an advantageous characteristic of these uses, the composition has a hardness of 20 to 2 000 gf, preferably of 20 to 900 gf and even better of 20 to 600 gf.

The invention also relates to a cosmetic method for facilitating the application of a cosmetic composition containing a liquid fatty phase, consisting in structuring the said fatty phase with a sufficient quantity of at least one polymer (homopolymer or copolymer) having a weight-average molecular mass ranging from 500 to 500 000, containing at least one moiety comprising:
- at least one polyorganosiloxane group, consisting of 1 to 1 000 organosiloxane units in the chain of the moiety or in the form of a graft, and
- at least two groups capable of establishing hydrogen interactions chosen from ester, amide, sulphonamide, carbamate, thiocarbamate, urea, urethane, thiourea, oxamido, guanidino and biguanidino groups, and combinations thereof, the polymer being solid at room temperature and soluble in the liquid fatty phase at a temperature of 25 to 250° C., and in adding at least one compound capable of lowering the enthalpy of fusion and possibly the melting temperature of the polymer to the composition.

The invention also relates to a cosmetic method for increasing the mass of a deposit of a cosmetic composition containing a liquid fatty phase consisting in structuring the said fatty phase with a sufficient quantity of at least one polymer (homopolymer or copolymer) having a weight-average molecular mass ranging from 500 to 500 000, containing at least one moiety comprising:
- at least one polyorganosiloxane group consisting of 1 to 1000 organosiloxane units in the chain of the moiety or in the form of a graft, and
- at least two groups capable of establishing hydrogen interactions, chosen from ester, amide, sulphonamide, carbamate, thiocarbamate, urea, urethane, thiourea, oxamido, guanidino and bioguanidino groups, and combinations thereof, the polymer being solid at room temperature and soluble in the liquid fatty phase at a temperature of 25 to 250° C., and in adding at least one compound capable of decreasing the enthalpy of fusion and possibly the melting temperature of the polymer to the composition.

The invention finally relates to the use, in a cosmetic composition or a physiologically acceptable composition comprising a continuous liquid fatty phase structured with at least one polymer (homopolymer or copolymer) having a weight-average molecular mass ranging from 500 to 500 000, containing at least one moiety comprising:
- at least one polyorganosiloxane group consisting of 1 to 1000 organosiloxane units in the chain of the moiety or in the form of a graft, and
- at least two groups capable of establishing hydrogen interactions, chosen from ester, amide, sulphonamide, carbamate, thiocarbamate, urea, urethane, thiourea, oxamido, guanidino and bioguanidino groups, and combinations thereof, the polymer being solid at room temperature and soluble in the liquid fatty phase at a temperature of 25 to 250° C., of a sufficient quantity of a compound capable of lowering the enthalpy of fusion and possibly the melting temperature of the polymer so as to facilitate the application of the said composition and increase the mass of a deposit of the said composition.

DETAILED DISCLOSURE OF THE INVENTION

The invention is illustrated in greater detail in the following examples of make-up formulation given by way of illustration and without limitation. The quantities are given as % by mass. The chemical compounds are given mainly as the CTFA ("International Cosmetic Ingredient Dictionary") name.

Example 1 (Comparative)

In this example not conforming to the invention, a makeup formula for the lips and the face was prepared exclusively from silicones with, as structuring agent, silicone polyamide and, as oil, a phenylated silicone.

The formula is then pigmented and cast in a pot.

The composition of the formula prepared is given below:

| Compound | % |
| --- | --- |
| Silicone polyamide of DP*45 obtained according to the teaching of patent US-5 981 680 | 25 |
| Phenylated silicone | 66.34 |
| Pigments | 8.66 |
| TOTAL | 100 |

*DP: degree of polymerization.

The silicone polymer is melted at 110° C. and mixed with a portion of the oil in order to obtain a liquid mixture. The pigments are ground in parallel in the remainder of the oil. Finally, the pigmented ground product is mixed with the oil plus gelling agent mixture at 110° C.

The deposit obtained on the hand from the stick is fine and nonhomogeneous.

In conclusion, it appears that the formula prepared in this comparative example is hard and deposits only very little colour during the application which is difficult.

Example 2

In this example in accordance with the invention, a makeup formula is prepared whose composition is similar to that of claim 1, except that 20% by mass of a compound according to the invention which lowers the melting temperature of the polymer, namely octadodecanol, is added to the formula.

The composition of the formula prepared is given below:

| Compound | % |
| --- | --- |
| Silicone polyamide of DP*45 obtained according to the teaching of patent US-5 981 680 | 25 |
| Octadodecanol | 20 |
| Phenylated silicone | 46.34 |
| Pigments | 8.66 |
| TOTAL | 100 |

*DP: degree of polymerization.

The silicone polymer is melted at 110° C. and mixed with part of the silicone oil and with the octadodecanol in order to obtain a liquid mixture. The pigments are ground in parallel in the remainder of the oil. Finally, the pigmented ground product is mixed with the oil plus gelling agent mixture at 110° C.

The appearance at room temperature of the 12.7 mm stick obtained after unmoulding is smooth, homogeneous and glossy.

The deposit obtained, prepared under the same conditions as in Example 1, is larger than that of Example 1.

The deposit is glossy.

In conclusion, by virtue of the presence of octadodecanol, the formula according to the invention is easier to apply and the deposit has a more intense colour, which allows the making up of the lips, for example. Moreover, an improvement is noted in the gloss of the product and of the deposit.

REFERENCES

[1] EP-A-1 068 856
[2] WO-A-01/97758
[3] U.S. Pat. No. 5,874,069
[4] U.S. Pat. No. 5,919,441
[5] U.S. Pat. No. 6,051,216
[6] WO-A-02/17870
[7] WO-A-02/17871
[8] EP-A-1 177 784
[9] U.S. Pat. No. 5,412,004
[10] EP-A-1 048, 686
[11] U.S. Pat. No. 5,981,680
[12] WO-A-99/06473
[13] U.S. Pat. No. 6,353,076

The invention claimed is:

1. A make-up cosmetic composition comprising:
at least one pigment and
a liquid continuous fatty phase comprising at least one structuring polymer and 5 to 25% by weight of the composition of at least one compound capable of reducing the enthalpy of fusion of the at least one structuring polymer which is a linear or a branched aliphatic monoalcohol having more than 8 carbon atoms but not more than 26 carbon atoms;
wherein the at least one structuring polymer has a weight-average molecular mass ranging from 500 to 500,000, is a solid at room temperature, and is soluble in the liquid fatty phase at a temperature of 25 to 250° C.; and
wherein the at least one structuring polymer comprises at least one moiety of formula (III) or (IV):

$$\left[ -\underset{O}{\overset{\parallel}{C}} - X - \left[ \underset{R^3}{\overset{R^1}{\underset{|}{Si}}O} \right]_m \underset{R^4}{\overset{R^2}{\underset{|}{Si}}} - X - \underset{O}{\overset{\parallel}{C}} - NH - Y - NH - \right]_n \quad \text{or} \quad (III)$$

$$\left[ -NH - X - \left[ \underset{R^3}{\overset{R^1}{\underset{|}{Si}}O} \right]_m \underset{R^4}{\overset{R^2}{\underset{|}{Si}}} - X - NH - \underset{O}{\overset{\parallel}{C}} - Y - \underset{O}{\overset{\parallel}{C}} - \right]_n \quad (IV)$$

in which:
1) $R^1$, $R^2$, $R^3$ and $R^4$, which may be identical or different, are selected from the group consisting of an A-substituent, a B-substituent, and a C-substituent:

wherein the A-substituent is a linear, branched or cyclic, saturated or unsaturated, $C_1$ to $C_{40}$ hydrocarbon, which optionally comprises in the chain of the hydrocarbon one or more of an oxygen atom, a sulphur atom, and a nitrogen atom, and optionally is partially or totally fluorinated;
wherein the B-substituent is a $C_6$ to $C_{10}$ aryl group, which is optionally substituted with one or more $C_1$ to $C_4$ alkyl groups, and
wherein the C-substituent is at least one polyorganosiloxane chain, which optionally comprises in the chain of the polyorganosiloxane one or more of an oxygen atom, a sulfur atom, and a nitrogen atom;
2) the groups X, which may be identical or different, represent a linear or branched $C_1$ to $C_{30}$ alkylenediyl group, which optionally comprises in the chain of the alkylenediyl group one or more oxygen atom and/or nitrogen atom;
3) Y is a saturated or unsaturated, $C_1$ to $C_{50}$ linear or branched divalent alkylene, arylene, cycloalkylene, alkylarylene or arylalkylene group, optionally comprising one or more oxygen atom, sulfur atom, and/or nitrogen atom, and/or bearing as substituent one of the following atoms or groups of atoms:
fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

$$R^5 - T \diagup_{\diagdown}$$

wherein
T represents a linear or branched, saturated or unsaturated, $C_3$ to $C_{24}$ trivalent or tetravalent hydrocarbon group optionally substituted with a polyorganosiloxane chain, and optionally comprising one or more atoms chosen from O, N and S, or
T represents a trivalent atom chosen from N, P and Al, and
$R^5$ represents a linear or branched $C_1$ to $C_{50}$ alkyl group or a polyorganosiloxane chain, optionally comprising one or more ester, amide, urethane, thiocarbamate, urea, thiourea and/or sulphonamide groups, which optionally is linked to another chain of the polymer; and
5) n is an integer ranging from 2 to 500, and m is an integer ranging from 1 to 1,000,
wherein the at least one pigment, the liquid fatty phase, the at least one structuring polymer, and the at least one compound capable of reducing the enthalpy of fusion of the at least one structuring polymer form a physiologically acceptable medium.

2. The composition according to claim 1, in which the liquid fatty phase further comprises at least one hydrocarbon oil.

3. The composition according to claim 1, wherein the liquid fatty phase further comprises at least one silicone oil.

4. The composition according to claim 3, wherein the liquid fatty phase comprises at least 30% by weight of silicone oil.

5. The composition according to claim 1, wherein the liquid fatty phase further comprises at least one volatile oil having a flash point ranging from 35 to 135° C.

6. The composition according to claim 5, wherein the volatile oil is selected from the group consisting of isododecane, isohexadecane, $C_8$-$C_{16}$ isoparaffins, isohexyl neopentanoate, isodecyl neopentanoate, and mixtures thereof.

7. The composition according to claim 5, wherein the volatile oil is selected from the group consisting of: isododecane, octyltrimethicone, hexyltrimethicone, decamethylcyclopentasiloxane D5, octamethylcyclotetrasiloxane D4, dodecamethylcyclohexasiloxane D6, heptamethyloctyltrisiloxane, decamethyltetrasiloxane, dodecamethylpentasiloxane, a polydimethylsiloxane having a viscosity of 1.5 cSt at 25° C., a polydimethyl-siloxane having a viscosity of 2 cSt at 25° C., a polydimethylsiloxane having a viscosity of 3 cSt at 25° C., a polydimethylsiloxane having a viscosity of 5 cSt at 25° C., and mixtures thereof.

8. The composition according to claim 5, wherein the volatile oil is selected from the group consisting of perfluoropolyethers, perfluoroalkanes, perfluoroadamantames, esters of perfluoroalkyl phosphates, fluorinated ester oils, and mixtures thereof.

9. The composition according to claim 5, wherein the at least one volatile oil ranges from 3 to 89.4% of the total weight of the composition.

10. The composition according to claim 1, wherein, the liquid fatty phase further comprises at least one volatile oil having a vapour pressure ranging from 0.01 to 300 mmHg, at 25° C.

11. The composition according to claim 1, wherein the liquid fatty phase further comprises a nonvolatile silicone oil.

12. The composition according to claim 1, wherein $R^1$, $R^2$, $R^3$ and $R^4$ represent, independently, a linear or branched $C_1$ to $C_{40}$ alkyl group.

13. The composition according to claim 1, wherein the at least one structuring polymer ranges from 0.5 to 80% of the total weight of the composition.

14. The composition according to claim 13, wherein the at least one structuring polymer ranges from 5 to 40% of the total weight of the composition.

15. The composition according to claim 1, wherein the liquid fatty phase ranges from 5 to 99% of the total weight of the composition.

16. The composition according to claim 1, wherein the at least one compound capable of reducing the enthalpy of fusion is present in an amount that reduces the enthalpy of fusion of the at least one structuring polymer.

17. The composition according to claim 16, wherein the reducing the enthalpy of fusion is by at least 3 J/g of the at least one structuring polymer.

18. The composition according to claim 16, wherein the at least one compound capable of reducing the enthalpy of fusion of the at least one structuring polymer is additionally capable of reducing the melting temperature of the at least one structuring polymer.

19. The composition according to claim 18, wherein the at least one compound is present in an amount that reduces the melting temperature of the at least one structuring polymer.

20. The composition according to claim 19, wherein the reducing of the melting temperature of the at least one structuring polymer is at least 3° C.

21. The composition according to claim 16, wherein the at least one compound capable of reducing the enthalpy of fusion and optionally the melting temperature of the at least one structuring polymer are compounds leading to a macroscopically homogeneous composition and/or which are soluble or dispersible in the fatty phase of the composition.

22. The composition according to claim 16, wherein the at least one compound reduces the enthalpy of fusion of the structuring polymer and the melting temperature of the at least one structuring polymer, and leads to a macroscopically homogeneous composition.

23. The composition according to claim 1, wherein the at least one compound is octyldodecanol.

24. The composition according to claim 23, wherein the amount of the at least one compound capable of reducing the enthalpy of fusion and optionally the melting temperature of the at least one structuring polymer ranges from 10 to 20% by weight.

25. The composition according to claim 1, wherein the amount of the at least one compound capable of reducing the enthalpy of fusion of the at least one structuring polymer ranges from 5 to 25% by weight.

26. The composition according to claim 1, wherein the mass ratio of the at least one structuring polymer to the at least one compound capable of reducing the enthalpy of fusion and optionally the melting temperature of the at least one structuring polymer ranges from 0.1 to 50.

27. The composition according to claim 1, which further comprises at least one cosmetic or dermatological active agent.

28. The composition according to claim 27, wherein the at least one dermatological active agent is selected from the group consisting of an essential oil, a vitamin, a moisturizer, a sunscreen, a cicatrizing agent, a ceramide, and mixtures thereof.

29. The composition according claim 1, which further comprises at least one additive selected from the group consisting of a filler, an antioxidant, a preservative perfume, and mixtures thereof.

30. The composition according to claim 1, wherein the at least one pigment is selected from the group consisting of zinc oxide, iron oxide, titanium oxide, and mixtures thereof.

31. The composition according to claim 1, which further comprises a dye.

32. The composition according to claim 1, wherein the composition is a transparent gel or of a transparent stick.

33. A mascara, an eyeliner, a foundation, a lipstick, a blusher, a make-up product for the body, an eyeshadow or a face powder, or a concealer product, which comprises the composition according to claim 1.

34. A cosmetic make-up method for the keratinous materials of human beings, comprising applying the cosmetic composition according to claim 1 to the keratinous material of said human being.

35. A mascara, an eyeliner, a foundation, a lipstick, a blusher, a make-up product for the body, an eyeshadow or a face powder, or a concealer product, which comprises the composition according to claim 1.

36. The composition according to claim 1, wherein the at least one compound capable of reducing the enthalpy of fusion of the at least one structuring polymer is a linear or a branched aliphatic monoalcohol having 12-26 carbon atoms.

37. The composition according to claim 36, wherein the amount of the at least one compound capable of reducing the enthalpy of fusion and optionally the melting temperature of the at least one structuring polymer ranges from 10 to 20% by weight.

38. The composition according to claim 1, wherein the amount of the at least one compound capable of reducing the enthalpy of fusion of the at least one structuring polymer ranges from 10 to 20% by weight.

39. The composition according to claim 1, wherein m is from 15 to 500.

40. The composition according to claim 1, wherein m is from 10 to 100.

41. The composition according to claim 1, wherein $R^1$, $R^2$, $R^3$ and $R^4$ are methyl groups, X is an (oxy)alkylene group containing from 1 to 20 carbon atoms, and Y is an alkylene group containing from 1 to 20 carbon atoms.

42. The composition according to claim 41, wherein m is from 15 to 500.

43. The composition according to claim 41, wherein m is from 10 to 100.

44. A make-up structured solid composition for the skin, the lips and/or the superficial body growths, comprising
at least one pigment in a sufficient quantity for applying make-up to the skin, the lips and/or the superficial body growths and
a liquid continuous fatty phase comprising at least one structuring polymer and 5 to 25% by weight of the composition of at least one compound capable of reducing the enthalpy of fusion of the at least one structuring polymer which is a linear or a branched aliphatic monoalcohol having more than 8 carbon atoms but not more than 26 carbon atoms;
wherein the at least one structuring polymer has a weight-average molecular mass ranging from 500 to 500,000, is a solid at room temperature, and is soluble in the liquid fatty phase at a temperature of 25 to 250° C.; and
wherein the at least one structuring polymer comprises at least one moiety of formula (III) or (IV):

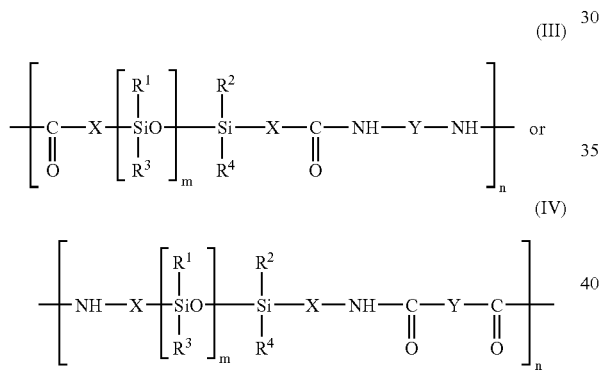

in which:
1) $R^1$, $R^2$, $R^3$ and $R^4$, which may be identical or different, are selected from the group consisting of an A-substituent, a B-substituent, and a C-substituent:
wherein the A-substituent is a linear, branched or cyclic, saturated or unsaturated, $C_1$ to $C_{40}$ hydrocarbon, which optionally comprises in the chain of the hydrocarbon one or more of an oxygen atom, a sulphur atom, and a nitrogen atom, and optionally is partially or totally fluorinated;
wherein the B-substituent is a $C_6$ to $C_{10}$ aryl group, which is optionally substituted with one or more $C_1$ to $C_4$ alkyl groups, and
wherein the C-substituent is at least one polyorganosiloxane chain, which optionally comprises in the chain of the polyorganosiloxane one or more of an oxygen atom, a sulfur atom, and a nitrogen atom;
2) the groups X, which may be identical or different, represent a linear or branched $C_1$ to $C_{30}$ alkylenediyl group, which optionally comprises in the chain of the alkylenediyl group one or more oxygen atom and/or nitrogen atom;
3) Y is a saturated or unsaturated, $C_1$ to $C_{50}$ linear or branched divalent alkylene, arylene, cycloalkylene, alkylarylene or arylalkylene group, optionally comprising one or more oxygen atom, sulfur atom, and/or nitrogen atom, and/or bearing as substituent one of the following atoms or groups of atoms:
fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

wherein
T represents a linear or branched, saturated or unsaturated, $C_3$ to $C_{24}$ trivalent or tetravalent hydrocarbon group optionally substituted with a polyorganosiloxane chain, and optionally comprising one or more atoms chosen from O, N and S, or
T represents a trivalent atom chosen from N, P and Al, and
$R^5$ represents a linear or branched $C_1$ to $C_{50}$ alkyl group or a polyorganosiloxane chain, optionally comprising one or more ester, amide, urethane, thiocarbamate, urea, thiourea and/or sulphonamide groups, which optionally is linked to another chain of the polymer; and
5) n is an integer ranging from 2 to 500, and m is an integer ranging from 1 to 1,000,
wherein the at least one pigment, the liquid fatty phase, the at least one structuring polymer, and the at least one compound capable of reducing the enthalpy of fusion of the at least one structuring polymer form a physiologically acceptable medium.

45. The composition according to claim 44, wherein the amount of the at least one compound capable of reducing the enthalpy of fusion and optionally the melting temperature of the at least one structuring polymer ranges from 10 to 20% by weight.

* * * * *